United States Patent
Xing et al.

(10) Patent No.: US 11,701,643 B2
(45) Date of Patent: *Jul. 18, 2023

(54) DEHYDROGENATION CATALYSTS AND METHODS FOR USING THEM

(71) Applicant: CLARIANT INTERNATIONAL LTD, Muttenz (CH)

(72) Inventors: Rong Xing, Louisville, KY (US); Vladimir Fridman, Louisville, KY (US)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/367,764

(22) Filed: Jul. 6, 2021

(65) Prior Publication Data

US 2022/0016604 A1 Jan. 20, 2022

Related U.S. Application Data

(60) Provisional application No. 63/053,781, filed on Jul. 20, 2020.

(51) Int. Cl.

| | |
|---|---|
| *B01J 23/56* | (2006.01) |
| *B01J 21/12* | (2006.01) |
| *B01J 23/89* | (2006.01) |
| *B01J 23/63* | (2006.01) |
| *B01J 23/656* | (2006.01) |
| *B01J 37/02* | (2006.01) |
| *B01J 37/08* | (2006.01) |
| *C07C 5/333* | (2006.01) |

(52) U.S. Cl.
CPC ............ *B01J 23/896* (2013.01); *B01J 21/12* (2013.01); *B01J 23/63* (2013.01); *B01J 23/6562* (2013.01); *B01J 37/024* (2013.01); *B01J 37/0205* (2013.01); *B01J 37/088* (2013.01); *C07C 5/3337* (2013.01); *C07C 2521/04* (2013.01); *C07C 2523/63* (2013.01); *C07C 2523/656* (2013.01); *C07C 2523/89* (2013.01)

(58) Field of Classification Search
CPC ... B01J 23/62; B01J 23/63; B01J 21/12; B01J 37/0018; B01J 37/0201; B01J 37/08; B01J 37/088; B01J 23/96; B01J 2523/00; B01J 2523/13; B01J 2523/25; B01J 2523/31; B01J 2523/32; B01J 2523/3706; B01J 2523/3712; B01J 2523/41; B01J 2523/828; C07C 5/3337; C07C 2521/04; C07C 2521/08; C07C 2521/12; C07C 2523/02; C07C 2523/04; C07C 2523/08; C07C 2523/10; C07C 2523/42; C07C 2523/58; C07C 2523/63; C07C 11/06; Y02P 20/52; Y02P 20/584
See application file for complete search history.

(56) References Cited

U.S. PATENT DOCUMENTS

| | | | |
|---|---|---|---|
| 3,198,749 A | 8/1965 | Gladrow | |
| 4,056,576 A | 11/1977 | Gregory | |
| 5,258,567 A | 11/1993 | Kerby | |
| 5,308,822 A | 5/1994 | Iezzi | |
| 5,346,871 A | 9/1994 | Robbins | |
| 5,414,182 A | 5/1995 | Iezzi | |
| 6,031,143 A | 1/2000 | Buonomo | |
| 7,235,706 B2 | 6/2007 | Iezzi | |
| 8,653,317 B2 | 2/2014 | Pierce | |
| 8,927,799 B2 | 1/2015 | Myers | |
| 9,776,170 B2 | 10/2017 | Kaminsky | |
| 10,933,405 B2 | 3/2021 | Fridman | |
| 11,021,419 B2 | 6/2021 | Xing | |
| 2004/0199034 A1* | 10/2004 | Walsdorff | C07C 5/48 585/310 |
| 2013/0178682 A1* | 7/2013 | Luo | B01J 23/825 585/660 |
| 2015/0202599 A1* | 7/2015 | Al-Zahrani | B01J 23/36 502/329 |

FOREIGN PATENT DOCUMENTS

| | | |
|---|---|---|
| CN | 102451677 | 5/2012 |
| WO | 201688093 | 6/2016 |
| WO | 2016088093 | 6/2016 |

* cited by examiner

*Primary Examiner* — In Suk C Bullock
*Assistant Examiner* — Jason Y Chong

(57) ABSTRACT

The present disclosure relates to gallium-based dehydrogenation catalysts that further include additional metal components, and to methods for dehydrogenating hydrocarbons using such catalysts. One aspect of the disclosure provides a calcined dehydrogenation catalyst that includes a gallium species, a cerium species, a platinum promoter, and a silica-alumina support. Optionally, the composition can include a promoter selected from the alkali metals and alkaline earth metals.

20 Claims, No Drawings

DEHYDROGENATION CATALYSTS AND METHODS FOR USING THEM

CROSS-REFERENCE TO RELATED APPLICATIONS

This application claims priority to U.S. Provisional Patent Application Ser. No. 63/053,781 filed Jul. 20, 2020, which is incorporated herein by reference in its entirety.

BACKGROUND OF THE DISCLOSURE

Field of the Disclosure

This disclosure relates generally to catalyst materials and methods for using them. More particularly, the present disclosure relates to gallium-based dehydrogenation catalysts that further include additional metal components, and to methods for dehydrogenating hydrocarbons using such catalysts.

Technical Background

Alkane dehydrogenation is a recognized process for production of a variety of useful hydrocarbon products, such as in the dehydrogenation of propane to make propene for use in the polymer industry, dehydrogenation of n-butane to produce n-butene or alkylate and butadiene useful in tire production, and the dehydrogenation of isobutane to make isobutylene suitable for conversion to methyl tert-butyl ether, isooctane, and alkylates to supplement and enrich gasolines. Current commercial catalysts useful for catalytic dehydrogenation of light alkanes include $CrO_x/Al_2O_3$ and $Pt—Sn/Al_2O_3$ catalysts, which have been in use for decades.

$CrO_x/Al_2O_3$ dehydrogenation catalysts typically contain a majority of their chromium in the Cr(III) oxidation state on the alumina surface. However, there typically remains a small amount of Cr(VI), which is carcinogenic and thus presents health risks during catalyst handling and operation. They also can cause significant environmental pollution.

Gallium-based dehydrogenation catalysts have been known for about two decades. They are generally not hazardous, and their application presents no significant environmental issue. However, these catalysts have limitations in activity, selectivity, and/or stability, especially for the commercially important dehydrogenation of propane.

Accordingly, there remains a need for dehydrogenation catalysts that provide improved activity, selectivity, and stability, without requiring the use of chromium, especially in the dehydrogenation of propane.

SUMMARY OF THE DISCLOSURE

The scope of the present disclosure is not affected to any degree by the statements within the summary.

In one aspect, the disclosure provides a dehydrogenation catalyst composition comprising Ga, present in the composition in an amount within the range of 0.5 wt. % to 20 wt. % (e.g., 1-20 wt. %, or 2-20 wt. %), calculated as elemental metal on a calcined basis;

Ce, present in the composition in an amount within the range of 0.2 wt. % to 20 wt. %, calculated as elemental metal on a calcined basis;

Pt, present in the composition in an amount within the range of 1 ppm to 500 ppm, calculated as elemental metal on a calcined basis;

optionally, a promoter M2 selected from the alkali metals, the alkaline earth metals, and any mixture thereof, present in the composition in an amount of up to 20 wt. %, calculated as elemental metal on a calcined basis; and a silica-alumina support S1, present in the composition in an amount within the range of 50 wt. % to 99 wt. %, calculated as oxide on a calcined basis, silica being present in S1 in an amount within the range of 1 wt. % to 30 wt. %, calculated as $SiO_2$ on a calcined basis.

In certain desirable embodiments, Ga is present in an amount of 2 to 10 wt. %, and Pt is present in an amount of 5 ppm to 400 ppm.

Another aspect of the disclosure is a method for dehydrogenating hydrocarbons, the method comprising contacting a hydrocarbon feed with a catalyst composition as described herein.

Other aspects of the disclosure will be apparent to the person of ordinary skill in the art in view of the disclosure herein.

DETAILED DESCRIPTION

In various aspects, the disclosure relates to dehydrogenation catalyst compositions that include gallium, cerium, a platinum promoter, and a silica-alumina support. Optionally, the composition can include a promoter selected from the alkali metals and alkaline earth metals. The disclosure demonstrates that such catalysts, which advantageously may be free of chromium-containing materials, can exhibit performance comparable to or even better than conventional, commercially available catalysts. The disclosure moreover demonstrates that such catalysts can exhibit activity and/or selectivity for $C_3$-$C_5$ hydrocarbon dehydrogenation, as well as long-term stability, better even than other gallium-based dehydrogenation catalysts.

Accordingly, one aspect of the disclosure provides a dehydrogenation catalyst composition. The catalyst composition includes Ga, present in the composition in an amount within the range of 0.5 wt. % to 20 wt. %, calculated as elemental metal on a calcined basis. The catalyst composition includes Ce, present in the composition in an amount within the range of 0.2 wt. % to 20 wt. %, calculated as elemental metal on a calcined basis. Without intending to be bound by theory, the inventors believe the Ga to be the primary catalytic species in dehydrogenation reactions. The catalyst composition further includes Pt, present in the composition in an amount within the range of 1 ppm to 500 ppm, calculated as elemental metal on a calcined basis. Without intending to be bound by theory, the inventors believe that Pt acts as a promoter for the catalytic species, especially Ga, and that Ce helps to stabilize the catalyst to allow for extended use at high conversion in dehydrogenation reactions. The catalyst composition optionally includes a promoter, M2, selected from the alkali metals, the alkaline earth metals, and any mixture thereof, present in the composition in an amount of up to 20 wt. %, calculated as elemental metal on a calcined basis. The catalyst composition includes a silica-alumina support, S1, present in the composition in an amount within the range of 50 wt. % to 99 wt. %, calculated as oxide on a calcined basis. And silica is present in S1 in an amount within the range of 1 wt. % to 30 wt. %, calculated as $SiO_2$ on a calcined basis.

As used herein, the terms "alumina" and "silica" include aluminum oxide and silicon oxide, respectively. As used herein, the term "oxide," including, e.g., "mixed oxide," "aluminum oxide," "silicon oxide," etc., includes oxides in all forms and crystalline phases. For example, "aluminum oxide" includes $Al_2O_3$, $Al_2O_x$ wherein x is within the range of 1 to 3, etc. Unless otherwise indicated, regardless of the actual stoichiometry of the oxide, oxides are calculated as the most stable oxide for purposes of weight percent determinations. For example, the person of ordinary skill in the art will appreciate that a non-stoichiometric oxide of aluminum, or even another form of aluminum, may still be calculated as $Al_2O_3$ for purposes of weight percent determinations. Moreover, unless otherwise indicated, the compositions are described on an as-calcined basis.

Without intending to be bound by theory, the present inventors believe that Ga acts as a primary catalytic species in dehydrogenation reactions mediated by the catalyst compositions described herein. In certain embodiments as otherwise described herein, Ga is present in the catalyst composition in an amount within the range of 0.5 wt. % to 17.5 wt. %, or 0.5 wt. % to 15 wt. %, or 0.5 wt. % to 12.5 wt. %, or 0.5 wt. % to 10 wt. %, 0.5 wt. % to 8.5 wt. %, or 0.5 wt. % to 7 wt. %, or 0.5 wt. % to 5 wt. %. In certain embodiments as otherwise described herein, Ga is present in the catalyst composition in an amount within the range of 0.5 wt. % to 10 wt. %, e.g., 0.5 wt. % to 8.5 wt. %, or 0.5 wt. % to 7 wt. %, or 0.5 wt. % to 5 wt. %, or 0.5 wt. % to 3 wt. %. In certain embodiments as otherwise described herein, Ga is present in the catalyst composition in an amount within the range of 0.5 wt. % to 10 wt. %, e.g., 0.5 wt. % to 8.5 wt. %, or 0.5 wt. % to 7 wt. %, or 0.5 wt. % to 5 wt. %, or 0.5 wt. % to 3 wt. %. In certain embodiments as otherwise described herein, Ga is present in the catalyst composition in an amount within the range of 1 wt. % to 10 wt. %, e.g., 1 wt. % to 8.5 wt. %, or 1 wt. % to 7 wt. %, or 1 wt. % to 5 wt. %, or 1 wt. % to 3 wt. %. In certain embodiments as otherwise described herein, Ga is present in the catalyst composition in an amount within the range of 1.5 wt. % to 10 wt. %, e.g., 1.5 wt. % to 8.5 wt. %, or 1.5 wt. % to 7 wt. %, or 1.5 wt. % to 5 wt. %, or 1.5 wt. % to 3 wt. %. In certain embodiments as otherwise described herein, Ga is present in the catalyst composition in an amount within the range of 2 wt. % to 10 wt. %, e.g., 2 wt. % to 8.5 wt. %, or 2 wt. % to 7 wt. %, or 2 wt. % to 5 wt. %, or 2 wt. % to 5 wt. %. In certain embodiments as otherwise described herein, Ga is present in the catalyst composition in an amount within the range of 3 wt. % to 10 wt. %, e.g., 3 wt. % to 8.5 wt. %, or 3 wt. % to 7 wt. %, or 3 wt. % to 5 wt. %, or 3 wt. % to 5 wt. %.

Without intending to be bound by theory, the present inventors believe that Ce helps to stabilize the catalyst compositions described herein. The inventors have noted that compositions lacking Ce tend to have lower stability over time under the conditions of the dehydrogenation reaction. In certain embodiments as otherwise described herein, Ce is present in the catalyst composition in an amount within the range of 0.2 wt. % to 15 wt. %, e.g., 0.2 wt. % to 10 wt. %, or 0.2 wt. % to 7 wt. %, or 0.2 wt. % to 5 wt. %, or 0.2 to 3 wt. %. In certain embodiments as otherwise described herein, Ce is present in the catalyst composition in an amount within the range of 0.5 wt. % to 20 wt. %, e.g., 0.5 wt. % to 15 wt. %, or 0.5 wt. % to 10 wt. %, or 0.5 wt. % to 7 wt. %, or 0.5 wt. % to 5 wt. %, or 0.5 wt. % to 3 wt. %. In certain embodiments as otherwise described herein, Ce is present in the catalyst composition in an amount within the range of 1 wt. % to 20 wt. %, e.g., 1 wt. % to 15 wt. %, or 1 wt. % to 10 wt. %, or 1 wt. % to 7 wt. %, or 1 wt. % to 5 wt. %, or 1 wt. % to 3 wt. %.

Without intending to be bound by theory, the inventors believe that Pt acts as a promoter for Ga and/or mixed Ga—Ce oxides. The present inventors note that, surprisingly, platinum-promoted gallium compounds present in the catalyst compositions described herein can remain active under dehydrogenation conditions for significantly longer than catalysts including platinum as a primary active species. In certain embodiments as otherwise described herein, Pt is present in the catalyst composition in an amount within the range of 5 ppm to 500 ppm, e.g., 25 ppm to 500 ppm, or 100 ppm to 500 ppm. In certain embodiments as otherwise described herein, Pt is present in the catalyst composition in an amount within the range of 1 ppm to 450 ppm, e.g., 5 ppm to 450 ppm, or 25 ppm to 450 ppm or 100 ppm to 450 ppm. In certain embodiments as otherwise described herein, Pt is present in the catalyst composition in an amount within the range of 1 ppm to 400 ppm, e.g., 5 ppm to 400 ppm, or 25 ppm to 400 ppm or 100 ppm to 400 ppm. In certain embodiments as otherwise described herein, Pt is present in the catalyst composition in an amount within the range of 1 ppm to 350 ppm, e.g., 5 ppm to 350 ppm, or 25 ppm to 350 ppm, or 100 ppm to 350 ppm. In certain embodiments as otherwise described herein, Pt is present in the catalyst composition in an amount within the range of 1 ppm to 300 ppm, e.g., 5 ppm to 300 ppm, or 25 ppm to 300 ppm, or 100 ppm to 300 ppm.

In certain embodiments as otherwise described herein, the catalyst composition includes a promoter M2 selected from the alkali metals, the alkaline earth metals, and any mixture thereof, present in the composition in an amount of up to 20 wt. %, calculated as elemental metal on a calcined basis. In certain embodiments, M2 is present in the composition in an amount of up to 17.5 wt. %, or up to 15 wt. %, or up to 10 wt. %, or up to 7.5 wt. %, or up to 5 wt. %, or up to 2.5 wt. %, or up to 2 wt. %, or up to 1.5 wt. %, or up to 1 wt. %, calculated as elemental metal on a calcined basis. For example, in certain embodiments, M2 is present in the composition in an amount within the range of 0.1 wt. % to 20 wt. %, or 0.1 wt. % to 17.5 wt. %, or 0.1 wt. % to 15 wt. %, or 0.1 wt. % to 12.5 wt. %, or 0.2 wt. % to 10 wt. %, or 0.2 wt. % to 7.5 wt. %, or 0.2 wt. % to 5 wt. %, or 0.2 wt. % to 2.5 wt. %, calculated as elemental metal on a calcined basis.

In certain desirable embodiments as otherwise described herein, M2 includes one or more alkali metals, the alkali metals being present in the composition in a combined amount within the range of 0.2 wt. % to 2.5 wt. %, calculated as elemental metal on a calcined basis. In certain such embodiments, M2 includes (e.g., is) K. In certain embodiments as otherwise described herein, M2 includes one or more alkali metals (e.g., including K), the alkali metals being present in the composition in a combined amount within the range of 0.2 wt. % to 2.25 wt. %, or 0.2 wt. % to 2 wt. %, or 0.2 wt. % to 1.75 wt. %, or 0.2 wt. % to 1.5 wt. %, or 0.2 wt. % to 1.25 wt. %, or 0.2 wt. % to 1 wt. %, or 0.2 wt. % to 0.75 wt. %, or 0.2 wt. % to 0.5 wt. %, calculated as elemental metal on a calcined basis.

In certain desirable embodiments as otherwise described herein, M2 includes one or more alkaline earth metals, the alkaline earth metals present in the composition in a combined amount within the range of 0.2 wt. % to 10 wt. %, calculated as elemental metal on a calcined basis. In certain such embodiments, M2 includes (e.g., is) Ba. In certain embodiments as otherwise described herein, M2 includes one or more alkaline earth metals (e.g., including Ba), the alkaline earth metals being present in the composition in a combined amount within the range of 0.2 wt. % to 9 wt. %, or 0.2 wt. % to 8 wt. %, or 0.2 wt. % to 7 wt. %, or 0.2 wt. % to 6 wt. %, or 0.2 wt. % to 5 wt. %, or 0.2 wt. % to 4 wt.

%, or 0.2 wt. % to 3 wt. %, or 0.2 wt. % to 2 wt. %, or 0.25 wt. % to 10 wt. %, or 0.5 wt. % to 10 wt. %, or 0.75 wt. % to 10 wt. %, or 1 wt. % to 10 wt. %, or 0.5 wt. % to 5 wt. %, or 0.5 wt. % to 2.5 wt. %, or 0.5 wt. % to 2 wt. %, or 0.5 wt. % to 1.5 wt. %, calculated as elemental metal on a calcined basis.

For example, in certain embodiments as otherwise described herein, M2 includes one or more alkali metals (e.g., K), the alkali metals being present in the composition in a combined amount within the range of 0.2 wt. % to 2.5 wt. % (e.g., 0.2 wt. % to 1 wt. %), and one or more alkaline earth metals (e.g., Ba), the alkaline earth metals being present in the composition in a combined amount within the range of 0.2 wt. % to 10 wt. % (e.g., 0.2 wt. % to 5 wt. %). In certain such embodiments, M2 includes (e.g., is) a mixture of K and Ba, and M2 is present in the composition in an amount within the range of 0.5 wt. % to 5 wt. %.

As described above, the catalyst composition comprises a silica-alumina support S1, silica being present in the support S1 in an amount within the range of 1 wt. % to 30 wt. %, calculated as $SiO_2$ on a calcined basis (i.e., as a fraction of the weight of the support). The person of ordinary skill in the art will appreciate that, as used herein, a "silica-alumina" support (e.g., S1) comprises a mixture of silica and alumina. The person of ordinary skill in the art will further appreciate that a "mixture" of silica and alumina includes homogeneous and heterogeneous mixtures. For example, the silica-alumina support S1 may comprise a covalently bound network including both silicon and aluminum atoms (e.g., —Si—O—Al—), and/or discrete domains of one or more of silica and alumina.

In certain embodiments as otherwise described herein, the amount of silica present in S1 is within the range of 1 wt. % to 27.5 wt. %, or 1 wt. % to 25 wt. %, or 1 wt. % to 22.5 wt. %, or 1 wt. % to 20 wt. %, or 1 wt. % to 17.5 wt. %, or 1 wt. % to 15 wt. %, or 1 wt. % to 12.5 wt. %, or 1 wt. % to 10 wt. %, or 2.5 wt. % to 30 wt. %, or 5 wt. % to 30 wt. %, or 7.5 wt. % to 30 wt. %, or 10 wt. % to 30 wt. %, or 15 wt. % to 30 wt. %, or 20 wt. % to 30 wt. %, or 2.5 wt. % to 25 wt. %, or 2.5 wt. % to 20 wt. %, or 2.5 wt. % to 15 wt. %, calculated as $SiO_2$ on a calcined basis. In certain embodiments as otherwise described herein, the amount of alumina present in S1 is within the range of 70 wt. % to 99 wt. %, calculated as $Al_2O_3$ on a calcined basis. In certain embodiments as otherwise described herein, the amount of alumina present in S1 is within the range of 72.5 wt. % to 99 wt. %, or 75 wt. % to 99 wt. %, or 77.5 wt. % to 99 wt. %, or 80 wt. % to 99 wt. %, or 82.5 wt. % to 99 wt. %, or 85 wt. % to 99 wt. %, or 87.5 wt. % to 99 wt. %, or 90 wt. % to 99 wt. %, or 70 wt. % to 97.5 wt. %, or 70 wt. % to 95 wt. %, or 70 wt. % to 92.5 wt. %, or 70 wt. % to 90 wt. %, or 70 wt. % to 85 wt. %, or 70 wt. % to 80 wt. %, or 75 wt. % to 97.5 wt. %, or 80 wt. % to 97.5 wt. %, or 85 wt. % to 97.5 wt. %, calculated as $Al_2O_3$ on a calcined basis. For example, in certain desirable embodiments as otherwise described herein, the amount of silica present in S1 is within the range of 2 wt. % to 20 wt. %, and the amount of alumina present in S1 is within the range of 80 wt. % to 98 wt. %, calculated as oxide on a calcined basis.

In certain embodiments as otherwise described herein, the total amount of alumina and silica in S1 is at least 80 wt. % of S1. For example, in certain embodiments as otherwise described herein, the total amount of alumina and silica in S1 is at least 85 wt. %, at least 90 wt. %, at least 92.5 wt. %, at least 95 wt. %, at least 97.5 wt. %, at least 98 wt. %, or at least 99 wt. % of S1, calculated as oxide on a calcined basis.

In certain embodiments as otherwise described herein, S1 is present in the composition in an amount within the range of 50 wt. % to 98 wt. %, e.g., 50 wt. % to 97.5 wt. %, or 50 wt. % to 95 wt. %, or 50 wt. % to 92.5 wt. %, or 50 wt. % to 90 wt. %, or 50 wt. % to 85 wt. %, or 50 wt. % to 80 wt. %, or 50 wt. % to 75 wt. %, or 60 wt. % to 99 wt. %, or 70 wt. % to 99 wt. %, or 80 wt. % to 99 wt. %, or 90 wt. % to 99 wt. %, or 95 wt. % to 99 wt. %, or 75 wt. % to 98 wt. %, or 80 wt. % to 97.5 wt. %, or 85 wt. % to 95 wt. %, calculated as oxide on a calcined basis.

The present inventors have surprisingly determined that one or more of La, Mn, Ti, Fe, Cu, Sn, W, Y and Zn can desirably improve the stability, activity, and/or selectivity of catalyst compositions described herein. Accordingly, in certain embodiments as otherwise described herein, the catalyst composition further comprises one or more of La, Mn, Ti, Fe, Cu, Sn, W, Y and Zn, present in the composition in a combined amount within the range of 0.01 wt. % to 10 wt. %, calculated as elemental metal on a calcined basis. For example, in certain embodiments as otherwise described herein, the catalyst composition further comprises one or more of La, Mn, Ti, Fe, Cu, Sn, and Zn.

In certain embodiments as otherwise described herein, the catalyst composition includes one or more of La, Mn, Ti, Fe, Cu, Sn, W, Y and Zn (e.g., one or more of La, Mn, Ti, Fe, Cu, Sn, and Zn) in an amount within the range of 0.01 wt. % to 9 wt. %, or 0.01 wt. % to 8 wt. %, or 0.01 wt. % to 7 wt. %, or 0.01 wt. % to 6 wt. %, or 0.01 wt. % to 5 wt. %, or 0.01 wt. % to 4 wt. %, or 0.01 wt. % to 3 wt. %, or 0.01 wt. % to 2 wt. %, or 0.05 wt. % to 10 wt. %, or 0.1 wt. % to 10 wt. %, or 0.25 wt. %, or 0.5 wt. % to 10 wt. %, or 0.75 wt. % to 10 wt. %, or 1 wt. % to 10 wt. %, or 1.5 wt. % to 10 wt. %, or 2 wt. % to 10 wt. %, or 3 wt. % to 10 wt. %, or 4 wt. % to 10 wt. %, or 5 wt. % to 10 wt. %, or 0.05 wt. % to 7.5 wt. %, or 0.05 wt. % to 5 wt. %, or 0.05 wt. % to 2.5 wt. %, calculated as elemental metal on a calcined basis.

For example, in certain desirable embodiments as otherwise described herein, the catalyst composition further comprises La, present in the composition in an amount within the range of 0.1 wt. % to 5 wt. %, calculated as elemental metal on a calcined basis. In another example, in certain desirable embodiments as otherwise described herein, the catalyst composition further comprises Ti, present in the composition in an amount within the range of 0.05 wt. % to 2 wt. %. In another example, in certain desirable embodiments as otherwise described herein, the catalyst composition further comprises Fe, present in the composition in an amount within the range of 0.025 wt. % to 1.5 wt. %. In another example, in certain desirable embodiments as otherwise described herein, the catalyst composition further comprises Sn, present in the composition in an amount within the range of 0.01 wt. % to 1 wt. %. In another example, in certain desirable embodiments as otherwise described herein, the catalyst composition further comprises Zn, present in the composition in an amount within the range of 1 wt. % to 6 wt. %.

In certain embodiments as otherwise described herein, Ga is present in the composition in an amount within the range of 1 wt. % to 5 wt. % (e.g., 2 wt. % to 5 wt. %), Ce is present in the composition in an amount within the range of 1 wt. % to 10 wt. % (e.g., 1 wt. % to 5 wt. %), Pt is present in the composition in an amount within the range of 10 ppm to 500 ppm (e.g., 10 ppm to 400 ppm), and S1 is present in the composition in an amount within the range of 80 wt. % to 99 wt. %. In certain such embodiments, silica is present in S1 in an amount within the range of 2 wt. % to 20 wt. %. In certain such embodiments, M2 includes (e.g., is) K, present in the composition in an amount within the range of 0.2 wt. % to 2.5 wt. %. In other such embodiments, M2 includes (e.g., is) a mixture of K and Ba, present in the composition in a combined amount within the range of 0.5 wt. % to 5 wt. %. In certain embodiments, the composition further comprises one or more of La, Mn, Ti, Fe, Cu, Sn, and Zn, present in the composition in a combined amount within the range of 0.01 wt. % to 10 wt. %.

For example, in certain embodiments as otherwise described herein, M2 includes (e.g., is) K, present in the composition in an amount within the range of 0.2 wt. % to 2.5 wt. %, and the composition further comprises La (e.g., present in an amount within the range of 0.5 wt. % to 2 wt. %), or Mn (e.g., present in an amount within the range of 0.5 wt. % to 2 wt. %), or Ti (e.g., present in an amount within the range of 0.05 wt. % to 1 wt. %). In other embodiments, M2 includes (e.g., is) a mixture of K and Ba, present in the composition in a combined amount within the range of 0.5 wt. % to 5 wt. %, and the composition further comprises Fe (e.g., present in an amount within the range of 0.05 wt. % to 1 wt. %), or Cu (e.g., present in an amount within the range of 0.05 wt. % to 1 wt. %), or Sn (e.g., present in an amount within the range of 0.01 wt. % to 0.5 wt. %), or La (e.g., present in an amount within the range of 0.5 wt. % to 2 wt. %), or Zn (e.g., present in an amount within the range of 1 wt. % to 3 wt. %).

In certain embodiments as otherwise described herein, Ga is present in the composition in an amount within the range of 2 wt. % to 5 wt. % (e.g., 3 wt. % to 5 wt. %), Ce is present in the composition in an amount within the range of 1 wt. % to 5 wt. %, Pt is present in the composition in an amount within the range of 100 ppm to 500 ppm (e.g., 100 ppm to 400 ppm), M2 is a mixture of K and Ba, present in the composition in a combined amount within the range of 0.5 wt. % to 5 wt. %, S1 is present in the composition in an amount within the range of 90 wt. % to 99 wt. %, and silica is present in S1 in an amount within the range of 2 wt. % to 20 wt. %. In certain embodiments, the composition further comprises La, present in the composition in an amount within the range of 0.1 wt. % to 5 wt. %.

In certain embodiments as otherwise described herein, Ga is present in the composition in an amount within the range of 2 wt. % to 5 wt. % (e.g., 3 wt. % to 5 wt. %), Ce is present in the composition in an amount within the range of 1 wt. % to 5 wt. %, Pt is present in the composition in an amount within the range of 100 ppm to 500 ppm (e.g., 100 ppm to 400 ppm), M2 is a mixture of K and Ba, present in the composition in a combined amount within the range of 1 wt. % to 5 wt. %, S1 is present in the composition in an amount within the range of 90 wt. % to 99 wt. %, and silica is present in S1 in an amount within the range of 2 wt. % to 20 wt. %.

In certain embodiments as otherwise described herein, Ga is present in the composition in an amount within the range of 2 wt. % to 5 wt. % (e.g., 3 wt. % to 5 wt. %), Ce is present in the composition in an amount within the range of 1 wt. % to 5 wt. %, Pt is present in the composition in an amount within the range of 100 ppm to 500 ppm (e.g., 100 ppm to 400 ppm), M2 is K, present in the composition in an amount within the range of 0.2 wt. % to 2.5 wt. %, S1 is present in the composition in an amount within the range of 90 wt. % to 99 wt. %, and silica is present in S1 in an amount within the range of 2 wt. % to 20 wt. %. In certain embodiments, the composition further comprises La, present in the composition in an amount within the range of 0.1 wt. % to 5 wt. %.

In certain embodiments as otherwise described herein, Ga is present in the composition in an amount within the range of 2 wt. % to 5 wt. % (e.g., 3 wt. % to 5 wt. %), Ce is present in the composition in an amount within the range of 1 wt. % to 5 wt. %, Pt is present in the composition in an amount within the range of 100 ppm to 500 ppm (e.g., 100 ppm to 400 ppm), M2 is K, present in the composition in an amount within the range of 0.2 wt. % to 2.5 wt. %, S1 is present in the composition in an amount within the range of 90 wt. % to 99 wt. %, and silica is present in S1 in an amount within the range of 2 wt. % to 20 wt. %. In certain embodiments, the composition further comprises Ti, present in the composition in an amount within the range of 0.05 wt. % to 2 wt. %.

In certain embodiments as otherwise described herein, Ga is present in the composition in an amount within the range of 2 wt. % to 5 wt. % (e.g., 3 wt. % to 5 wt. %), Ce is present in the composition in an amount within the range of 1 wt. % to 5 wt. %, Pt is present in the composition in an amount within the range of 100 ppm to 500 ppm (e.g., 100 ppm to 400 ppm), M2 is a mixture of K and Ba, present in the composition in a combined amount within the range of 1 wt. % to 5 wt. %, S1 is present in the composition in an amount within the range of 90 wt. % to 99 wt. %, and silica is present in S1 in an amount within the range of 2 wt. % to 20 wt. %. In certain embodiments, the composition further comprises Fe, present in the composition in an amount within the range of 0.025 wt. % to 1.5 wt. %.

In certain embodiments as otherwise described herein, Ga is present in the composition in an amount within the range of 2 wt. % to 5 wt. % (e.g., 3 wt. % to 5 wt. %), Ce is present in the composition in an amount within the range of 1 wt. % to 5 wt. %, Pt is present in the composition in an amount within the range of 100 ppm to 500 ppm (e.g., 100 ppm to 400 ppm), M2 is a mixture of K and Ba, present in the composition in a combined amount within the range of 1 wt. % to 5 wt. %, S1 is present in the composition in an amount within the range of 90 wt. % to 99 wt. %, and silica is present in S1 in an amount within the range of 2 wt. % to 20 wt. %. In certain embodiments, the composition further comprises Sn, present in the composition in an amount within the range of 0.01 wt. % to 1 wt. %

In certain embodiments as otherwise described herein, Ga is present in the composition in an amount within the range of 2 wt. % to 5 wt. % (e.g., 3 wt. % to 5 wt. %), Ce is present in the composition in an amount within the range of 1.5 wt. % to 5.5 wt. %, Pt is present in the composition in an amount within the range of 100 ppm to 500 ppm (e.g., 100 ppm to 400 ppm), M2 is K, present in the composition in an amount within the range of 0.2 wt. % to 2.5 wt. %, S1 is present in the composition in an amount within the range of 90 wt. % to 99 wt. %, and silica is present in S1 in an amount within the range of 2 wt. % to 20 wt. %. In certain embodiments, the composition further comprises La, present in the composition in an amount within the range of 0.1 wt. % to 5 wt. %.

In certain embodiments as otherwise described herein, Ga is present in the composition in an amount within the range of 2 wt. % to 5 wt. % (e.g., 3 wt. % to 5 wt. %), Ce is present in the composition in an amount within the range of 1 wt. % to 5 wt. %, Pt is present in the composition in an amount within the range of 100 ppm to 500 ppm (e.g., 100 ppm to 400 ppm), M2 is a mixture of K and Ba, present in the composition in a combined amount within the range of 1 wt. % to 5 wt. %, S1 is present in the composition in an amount within the range of 90 wt. % to 99 wt. %, and silica is present in S1 in an amount within the range of 2 wt. % to 20 wt. %.

In certain embodiments, the composition further comprises Zn, present in the composition in an amount within the range of 1 wt. % to 6 wt. %.

The person of ordinary skill in the art will appreciate that the catalyst composition may, in some embodiments as otherwise described herein, be substantially free of Cr. Chromium-free compositions are especially desirable from an environmental perspective. For example, in certain embodiments as otherwise described herein, the catalyst composition includes less than 1 wt. %, or less than 0.9 wt. %, or less than 0.8 wt. %, or less than 0.7 wt. %, or less than 0.6 wt. %, or less than 0.5 wt. %, or less than 0.4 wt. %, or less than 0.3 wt. %, or less than 0.2 wt. %, or less than 0.1 wt. %, or less than 0.05 wt. %, or less than 0.01 wt. % of Cr, calculated as oxide on a calcined basis.

The present inventors have determined that suitable dehydrogenation catalysts can be made using the Ga, Ce, Pt, S1 and optional M2 components described herein, e.g., in some embodiments without the use of other promotor or catalytic species (e.g., other than La, Mn, Ti, Fe, Cu, Sn, W, Y, and Zn). Accordingly, in certain embodiments as otherwise described herein, the total amount of Ga, Ce, Pt, M2 and S1 is at least 80 wt. %, e.g., at least 85 wt. %, or at least 87 wt. %, or at least 90 wt. % of the composition (i.e., Ga, Ce, Pt, and M2 calculated as elemental metal and S1 calculated as oxide on a calcined basis). In certain desirable embodiments as otherwise described herein, the total amount of Ga, Ce, Pt, M2, S1, and any of La, Mn, Ti, Fe, Cu, Sn, W, Y, and Zn present in the composition is at least 85 wt. %, e.g., at least 87 wt. %, or at least 90 wt. %, or at least 92.5 wt. %, or at least 95 wt. %, or at least 97.5 wt. %, or at least 98 wt. % of the composition (i.e., Ga, Ce, Pt, M2, and any of La, Mn, Ti, Fe, Cu, Sn, W, Y, and Zn calculated as elemental metal and S1 calculated as oxide on a calcined basis).

In certain desirable embodiments as otherwise described herein, the support S1 comprises a covalent network structure, throughout which structure one or more of the Ga, Ce, promoters (e.g., Pt and M2), and additional elements (e.g., La, Mn, Ti, Fe, Cu, Sn, W, Y, and/or Zn) are dispersed. In other embodiments, the Ga, Ce, promoters and additional elements are substantially disposed on surfaces of the support S1.

Another aspect of the disclosure is a method for preparing a dehydrogenation catalyst composition as described herein. Conventional methods can be adapted for use in preparing the dehydrogenation catalysts of the disclosure. For example, various hydrolysis-polycondensation, precipitation and impregnation processes can be used, singly or in combination, to provide the compositions. Silica-alumina support materials can suitably be made, for example, by a hydrolysis-polycondensation process (e.g., from one or more hydroxide or oxy compounds). Certain of the Ga, Ce, Pt and M2 species can be formulated together with the silica-alumina support through hydrolysis-polycondensation. Ga, Ce, Pt and M2 species can alternatively or additionally be provided to the support through impregnation. Similarly, certain of La, Mn, Ti, Fe, Cu, Sn, W, Y, and Zn species can be formulated together with the silica-alumina support through hydrolysis-polycondensation, or alternatively or additional can be provided to the support through impregnation.

For example, in certain embodiments, a method for making a dehydrogenation catalyst as described herein includes providing a silica-alumina support S1 (e.g., the product of a hydrolysis-polycondensation reaction of one or more silicon and aluminum oxy compounds), impregnating the silica-alumina support S1 with Ga, Ce, Pt and M2 via one or more impregnation steps to provide the desired amounts of Ga, Ce, Pt and M2 in the final catalyst. In each such impregnation step, an impregnation solution (e.g., an aqueous impregnation solution) containing one or more of a Ga source, a Ce source, an Pt source, an M2 source, and a source of La, Mn, Ti, Fe, Cu, Sn, W, Y, and Zn, is contacted with the support. After removal of the solution from the impregnated support, it can be dried and/or calcined. In certain such embodiments, providing the silica-alumina support S1 comprises reacting one or more S1 sources, e.g., in a hydrolysis-polycondensation reaction, with the S1 sources being one or more oxy compounds, e.g., oxides (e.g., alumina, silica), alkoxides (e.g., tetraethyl orthosilicate, aluminum isopropoxide), oxynitrates, nitrates, acetylacetonates, or hydroxides (e.g., aluminum hydroxide). The amounts and identities of the various components (e.g., Ga, Ce, Pt, M2, S1, La, Mn, Ti, Fe, Cu, Sn, W, Y, and Zn) can be as otherwise described above with respect to the catalyst composition of the disclosure (i.e., measured with respect to final catalyst composition).

In another example, in certain embodiments, the method includes reacting an S1 source (e.g., as otherwise described herein) in the presence of one or more of a Ga source, a Ce source, a Pt source, an M2 source, and a source of La, Mn, Ti, Fe, Cu, Sn, W, Y, and Zn, and calcining the reaction product to provide an silica-alumina support S1 formulated with one or more of Ga, Ce, Pt, M2, La, Mn, Ti, Fe, Cu, Sn, W, Y, and Zn. One or more of a Ga source, a Ce source, a Pt source, an M2 source, and a source of La, Mn, Ti, Fe, Cu, Sn, W, Y, and/or Zn, can then be provided to the calcined reaction product via one or more impregnation steps to provide the desired amounts of Ga, Ce, Pt, M2, La, Mn, Ti, Fe, Cu, Sn, W, Y, and Zn in the final catalyst (i.e., each coming from being formulated together with the support, added via impregnation, or a combination thereof). The amounts and identities of the various components (e.g., Ga, Ce, Pt, M2, S1, La, Mn, Ti, Fe, Cu, Sn, W, Y, and Zn) can be as otherwise described above with respect to the catalyst composition of the disclosure.

In certain embodiments as otherwise described herein, the method comprises impregnating a silica-alumina support S1 with an impregnation solution comprising a gallium salt to form a Ga-formulated support S1. In other embodiments as otherwise described herein, the method comprises reacting an S1 source in the presence of a Ga source, for example, by acidifying an aqueous mixture of aluminum hydroxide, silica, and gallium (e.g., in the form of a nitrate, isopropoxide or acetylacetonate) and calcining the reaction product to provide a silica-alumina support S1 formulated with Ga.

In certain embodiments as otherwise described herein, the method comprises impregnating a silica-alumina support S1 with an impregnation solution comprising a cerium salt to provide a Ce-formulated support S1. In other embodiments, the method comprises reacting an S1 source in the presence of a Ce source, for example, by acidifying an aqueous mixture of aluminum hydroxide, silica, gallium (e.g., in the form of a nitrate, isopropoxide or acetylacetonate) and cerium (e.g., in the form of isopropoxide, acetylacetonate or nitrate), and calcining the reaction product to provide a silica-alumina support S1 formulated with Ce.

In certain embodiments as otherwise described herein, the method comprises reacting an S1 source in the presence of a Ga source and a Ce source, for example, by acidifying an aqueous mixture of aluminum hydroxide, silica, cerium (e.g., in the form of isopropoxide, acetylacetonate or nitrate), and calcining the reaction product to provide a silica-alumina support S1 formulated with gallium and cerium.

In certain embodiments, a method for preparing a dehydrogenation catalyst as described herein includes providing a silica-alumina support S1 formulated with Ga. The formulation with Ga can be through an initial impregnation step, or through reaction of a Ga source together with the S1 source(s). The Ga-formulated silica-alumina support S1 can be impregnated with Ce, Pt, M2, and/or La, Mn, Ti, Fe, Cu, Sn, W, Y, or Zn (e.g., using an impregnation solution comprising a Ce source, an Pt source, an M2 source, and/or a source of La, Mn, Ti, Fe, Cu, Sn, W, Y, or Zn). The impregnated material can then be calcined.

In certain embodiments, a method for preparing a dehydrogenation catalyst as described herein includes providing a silica-alumina support S1 formulated with Ga and Ce. The formulation with Ga and Ce can be through an initial impregnation step, or through reaction of Ga source and Ce sources together with the S1 source(s). The Ga and Ce-formulated silica-alumina support S1 can be impregnated with Pt, M2, and/or one or more of La, Mn, Ti, Fe, Cu, Sn, W, Y, or Zn (e.g., using an impregnation solution comprising an Pt source, an M2 source, and/or a source of La, Mn, Ti, Fe, Cu, Sn, W, Y, or Zn). The impregnated material can then be calcined.

In certain embodiments as otherwise described herein, the Ga source is a gallium salt, e.g., gallium nitrate, gallium isopropoxide, or gallium acetylacetonate.

In certain embodiments as otherwise described herein, the Ce source is a cerium salt, e.g., cerium nitrate, cerium isopropoxide or cerium acetylacetonate.

In certain embodiments as otherwise described herein, the Pt source is a salt. For example, in certain embodiments as otherwise described herein, the Pt source is a platinum salt, e.g., $Pt(NH_3)_4(NO_3)_2$ or $H_2PtCl_4$.

In certain embodiments as otherwise described herein, the M2 source is a salt. For example, in certain embodiments as otherwise described herein, the M2 source is a salt of a group 1 element, e.g., $KNO_3$. In another example, in certain embodiments as otherwise described herein, the M2 source is a salt of a group 2 element, e.g., $Mg(NO_3)_2$, $Ca(NO_3)_2$, $Sr(NO_3)_2$, or $Ba(NO_3)_2$.

In certain embodiments as otherwise described herein, the source of one or more of La, Mn, Ti, Fe, Cu, Sn, W, Y, and Zn is a salt. For example, in certain embodiments as otherwise described herein, the source is $La(NO_3)_2 \cdot 6H_2O$, $Mn(NO_3)_2 \cdot 4H_2O$, $Fe(NO_3)_3 \cdot 9H_2O$, $FeSO_4 \cdot 7H_2O$, $Cu(NO_3)_3 \cdot 5H_2O$, $SnCl_4 \cdot 4H_2O$, $Zn(NO_3)_2$, or an organic titanate.

While particular salt species have been described above, the person of ordinary skill in the art will appreciate that other salts and other metallic can be used in the methods described herein.

As described above, the method includes calcining the impregnated silica-alumina support S1. In certain embodiments as otherwise described herein, the impregnated silica-alumina support S1 is calcined at a temperature within the range of 300° C. to 1,200° C. For example, in certain embodiments, the impregnated support S1 is calcined at a temperature within the range of 350° C. to 1,200° C., or 400° C. to 1,200° C., or 450° C. to 1,200° C., or 500° C. to 1,200° C., or 550° C. to 1,200° C., or 300° C. to 1,150° C., or 300° C. to 1,100° C., or 300° C. to 1,050° C., or 300° C. to 1,000° C., or 300° C. to 950° C., or 350° C. to 1,150° C., or 400° C. to 1,000° C., or 450° C. to 900° C.

In certain embodiments as otherwise described herein, the impregnated silica-alumina support S1 is calcined for a period of time within the range of 5 min. to 12 hr. For example, in certain embodiments as otherwise described herein, the impregnated support S1 is calcined for a period of time within the range of 10 min. to 12 hr., or 15 min. to 12 hr., or 20 min. to 12 hr., or 30 min. to 12 hr., or 45 min. to 12 hr., or 1 hr. to 12 hr., or 1.5 hr. to 12 hr., or 2 hr. to 12 hr., or 5 min. to 11 hr., or 5 min. to 10 hr., or 5 min. to 9 hr., or 5 min. to 8 hr., or 5 min. to 7.5 hr., or 5 min. to 7 hr., or 5 min. to 6.5 hr., or 5 min. to 6 hr., or 5 min. to 5.5 hr., or 5 min. to 5 hr., or 30 min. to 11 hr., or 1 hr. to 10 hr., or 1.5 hr. to 9 hr., or 2 hr. to 8 hr., or 2 hr. to 6 hr., or 2 hr. to 4 hr.

In certain embodiments as otherwise described herein, the impregnated silica-alumina support S1 is dried before calcination. In certain embodiments as otherwise described herein, the impregnated support S1 is dried at a temperature within the range of 50° C. to 250° C. For example, in certain embodiments as otherwise described herein, the impregnated support S1 is dried at a temperature within the range of 50° C. to 220° C., or 50° C. to 200° C., or 50° C. to 180° C., or 100° C. to 240° C., or 120° C. to 240° C., or 140° C. to 240° C., or 100° C. to 220° C., or 120° C. to 200° C., or 140° C. to 180° C.

In certain embodiments as otherwise described herein, the impregnated silica-alumina support S1 is dried for a period of time within the range of 30 min. to 36 hr. For example, in certain embodiments as otherwise described herein, the impregnated support S1 is dried for a period of time within the range of 30 min. to 30 hr., or 30 min. to 24 hr., or 30 min. to 22 hr., or 30 min. to 20 hr., or 1 hr. to 36 hr., or 2 hr. to 36 hr., or 3 hr. to 36 hr., or 4 hr. to 36 hr., or 1 hr. to 30 hr., or 1 hr. to 24 hr., or 2 hr. to 22 hr., or 2 hr. to 20 hr.

Another aspect of the disclosure is a catalyst composition prepared by a method as described herein.

Advantageously, the present inventors have determined that the use of catalyst compositions described herein can catalyze a hydrocarbon dehydrogenation reaction at an efficiency comparable to or better than conventional, commercially available catalyst materials. The present inventors have moreover determined that such catalysts can exhibit activity and/or selectivity for $C_3$-$C_5$ hydrocarbon dehydrogenation, as well as long-term stability, better even than other gallium-based dehydrogenation catalysts.

The compositions described herein are especially useful in hydrocarbon dehydrogenation reactions. Accordingly, another aspect of the disclosure is a method for dehydrogenating alkanes that includes contacting a hydrocarbon feed with a catalyst composition as described herein under conditions sufficient to cause hydrocarbon dehydrogenation. For example, the methods described can be used in the dehydrogenation of light paraffins.

In some embodiments as otherwise described herein, the hydrocarbon feed comprises one or more $C_3$-$C_5$ alkanes. For example, in certain embodiments as otherwise described herein, the hydrocarbon feed comprises propane.

A dehydrogenation process as described herein can be performed at a variety of conversions. For example, in certain embodiments as otherwise described herein, the process is operated at a conversion of at least 25 wt. %, e.g., at least 30 wt. % at least 40 wt. %, or even at least 45 wt. %. In certain embodiments, the process is operated at a conversion in the range of 25-70 wt. %, e.g., 25-60 wt. %, or 25-50 wt. %, or 30-70 wt. %, or 30-60 wt. %, or 30-50 wt. %, or 40-70 wt. %, or 40-65 wt. %, or 40-50 wt. %, or 45-70 wt. %, or 45-65 wt. %, or 45-55 wt. %.

A dehydrogenation process as described herein can be performed at a variety of selectivities. For example, in certain embodiments as otherwise described herein, the process is operated at a selectivity (i.e., for monodehydrogenated product, e.g., propylene from propane) of at least 80 wt. %, e.g., at least 85 wt. %, or even at least 90 wt. %. In certain embodiments, the process is operated at a selectivity in the range of 80-95 wt. %, e.g., 80-90 wt. %, or 85-95 wt. %, or 85-90 wt. %, or 90-95 wt. %.

In certain embodiments, the yield of the process (i.e., the product of the conversion and the selectivity) is in the range of 25-55 wt. %, e.g., 25-50 wt. %, or 25-45 wt. %, or 30-55 wt. %, or 30-45 wt. %, or 30-40 wt. %, or 35-55 wt. %, or 35-50 wt. %, or 35-45 wt. %, or 40-55 wt. %, or 40-50 wt. %.

The contacting of the feed with the catalyst compositions described herein can be conducted in a variety of ways familiar to the person of ordinary skill in the art. Conventional equipment and processes can be used in conjunction with the catalyst compositions of the disclosure to provide beneficial performance. Thus, the catalyst may be contained in one bed within a reactor vessel or divided up among a plurality of beds within a reactor. The reaction system may contain one or more reaction vessels in series. The feed to the reaction zone can flow vertically upwards, or downwards through the catalyst bed in a typical plug flow reactor, or horizontally across the catalyst bed in a radial flow type reactor.

The contacting of the feed with the catalyst composition can be performed using conventional methods. For example, the feed may be introduced into the reaction zone containing the catalyst composition at a constant rate, or alternatively, at a variable rate.

In certain embodiments as otherwise described herein, the feed is contacted with the provided catalyst composition at a liquid hourly space velocity (LHSV) within the range of $0.5\ h^{-1}$ to $4\ h^{-1}$. For example, in certain embodiments as otherwise described herein, the feed is contacted with the provided catalyst composition at a liquid hourly space velocity of $0.75\ h^{-1}$ to $4\ h^{-1}$, or $1\ h^{-1}$ to $4\ h^{-1}$, or $1.25\ h^{-1}$ to $4\ h^{-1}$, or $1.5\ h^{-1}$ to $4\ h^{-1}$, or $0.5\ h^{-1}$ to $3.75\ h^{-1}$, or $0.5\ h^{-1}$ to $3.5\ h^{-1}$, or $0.5\ h^{-1}$ to $3.25\ h^{-1}$, or $0.5\ h^{-1}$ to $3\ h^{-1}$, or $0.5\ h^{-1}$ to $2.75\ h^{-1}$, or $0.5\ h^{-1}$ to $2.5\ h^{-1}$, or $0.75\ h^{-1}$ to $3.5\ h^{-1}$, or $1\ h^{-1}$ to $3\ h^{-1}$, or $1.25\ h^{-1}$ to $2.75\ h^{-1}$, or $1.5\ h^{-1}$ to $2.5\ h^{-1}$.

In certain embodiments as otherwise described herein, the method is carried out at a temperature within the range of 400° C. to 850° C. For example, in certain embodiments as otherwise described herein, the method is carried out at a temperature within the range of 400° C. to 800° C., or 400° C. to 750° C., or 400° C. to 700° C., or 400° C. to 650° C., or 450° C. to 850° C., or 500° C. to 850° C., or 550° C. to 850° C., or 600° C. to 850° C., or 450° C. to 800° C., or 500° C. to 750° C.

In certain embodiments as otherwise described herein, the method is carried out at a pressure within the range of 0.1 bar to 1 bar. For example, in certain embodiments as otherwise described herein, the method is carried out at a pressure within the range of 0.1 bar to 0.9 bar, or 0.1 bar to 0.8 bar, or 0.1 bar to 0.7 bar, or 0.1 bar to 0.6 bar, or 0.1 bar to 0.5 bar, or 0.2 bar to 1 bar, or 0.3 bar to 1 bar, or 0.4 bar to 1 bar, or 0.5 bar to 1 bar, or about 0.2 bar to 0.9 bar, or 0.3 bar to 0.8 bar, or 0.4 bar to 0.7 bar.

EXAMPLES

The Examples that follow are illustrative of specific embodiments of the invention, and various uses thereof. They are set forth for explanatory purposes, only, and are not to be taken as limiting the invention.

Example 1. Catalyst Preparation

An $Al_2O_3$ support was impregnated with an aqueous solution of $Ga(NO_3)_3$, $Pt(NH_3)_4(NO_3)_2$, and $KNO_3$ by incipient wetness. The impregnated support was dried in air at room temperature for at least 1 hour, then dried in air at 338° F. for 1 hour, and then calcined in air at 1382° F. for 1 hour to provide comparative catalyst C1 comprising 3.0 wt. % Ga, 0.025 wt. % Pt, and 0.35 wt. % K.

An $Al_2O_3$—$SiO_2$ support including 10% $SiO_2$ (Sasol Siralox 10) was impregnated with an aqueous solution of $Ga(NO_3)_3$, $Pt(NH_3)_4(NO_3)_2$, and $KNO_3$ by incipient wetness. The impregnated support was dried in air at room temperature for at least 1 hour, then dried in air at 338° F. for 1 hour, and then calcined in air at 1382° F. for 1 hour, to provide comparative catalyst C2 comprising 4.5 wt. % Ga, 0.02 wt. % Pt, and 0.25 wt. % K.

An $Al_2O_3$—$SiO_2$ support including 10% $SiO_2$ (Sasol Siralox 10) was impregnated with an aqueous solution of $Ga(NO_3)_3$, $Pt(NH_3)_4(NO_3)_2$, $KNO_3$, and $Ce(NO_3)_3 \cdot 6H_2O$ by incipient wetness. The impregnated support was dried in air at room temperature for at least 1 hour, then dried in air at 338° F. for 1 hour, and then calcined in air at 1382° F. for 1 hour, to provide catalyst A1 comprising 4.5 wt. % Ga, 0.02 wt. % Pt, 0.25 wt. % K, and 1.0 wt. % Ce.

An $Al_2O_3$—$SiO_2$ support including 10% $SiO_2$ (Sasol Siralox 10) was impregnated with an aqueous solution of $Ga(NO_3)_3$, $Pt(NH_3)_4(NO_3)_2$, $KNO_3$, $Ce(NO_3)_3 \cdot 6H_2O$, and $Ba(NO_3)_2$ by incipient wetness. The impregnated support was dried in air at room temperature for at least 1 hour, then dried in air at 338° F. for 1 hour, and then calcined in air at 1382° F. for 1 hour, to provide catalyst A2 comprising 4.5 wt. % Ga, 0.02 wt. % Pt, 0.25 wt. % K, 1 wt. % Ce, and 1 wt. % Ba.

An $Al_2O_3$—$SiO_2$ support including 10% $SiO_2$ (Sasol Siralox 10) was impregnated with an aqueous solution of $Ga(NO_3)_3$, $Pt(NH_3)_4(NO3)_2$, $KNO_3$, $Ce(NO_3)_3 \cdot 6H_2O$, and $La(NO_3)_2 \cdot 6H_2O$ by incipient wetness. The impregnated support was dried in air at room temperature for at least 1 hour, then dried in air at 338° F. for 1 hour, and then calcined in air at 1382° F. for 1 hour, to provide catalyst A3 comprising 4.5 wt. % Ga, 0.02 wt. % Pt, 0.25 wt. % K, 1 wt. % Ce, and 1.2 wt. % La.

An $Al_2O3$—$SiO_2$ support including 10% $SiO_2$ (Sasol Siralox 10) was impregnated with an aqueous solution of $Ga(NO_3)_3$, $Pt(NH_3)_4(NO_3)_2$, $KNO_3$, $Ce(NO_3)_3 \cdot 6H_2O$, and $Mn(NO_3)_2 \cdot 4H_2O$ by incipient wetness. The impregnated support was dried in air at room temperature for at least 1 hour, then dried in air at 338° F. for 1 hour, and then calcined in air at 1382° F. for 1 hour, to provide catalyst A4 comprising 4.5 wt. % Ga, 0.02 wt. % Pt, 0.25 wt. % K, 1 wt. % Ce, and 1 wt. % Mn.

An $Al_2O_3$—$SiO_2$ support including 10% $SiO_2$ (Sasol Siralox 10) was impregnated with an aqueous solution of $Ga(NO_3)_3$, $Pt(NH_3)_4(NO_3)_2$, $KNO_3$, $Ce(NO_3)_3 \cdot 6H_2O$, and an organic titanate (Tyzor™) by incipient wetness. The impregnated support was dried in air at room temperature for at least 1 hour, then dried in air at 338° F. for 1 hour, and then calcined in air at 1382° F. for 1 hour, to provide catalyst A5 comprising 4.5 wt. % Ga, 0.02 wt. % Pt, 0.25 wt. % K, 1 wt. % Ce, and 0.3 wt. % Ti.

An $Al_2O_3$—$SiO_2$ support including 10% $SiO_2$ (Sasol Siralox 10) was impregnated with an aqueous solution of $Ga(NO_3)_3$, $Pt(NH_3)_4(NO_3)_2$, $KNO_3$, $Ce(NO_3)_3 \cdot 6H_2O$, $Ba(NO_3)_2$ and $Fe(NO_3)_3 \cdot 9H_2O$ by incipient wetness. The impregnated support was dried in air at room temperature for at least 1 hour, then dried in air at 338° F. for 1 hour, and then calcined in air at 1382° F. for 1 hour, to provide catalyst A6 comprising 4.5 wt. % Ga, 0.02 wt. % Pt, 0.25 wt. % K, 1 wt. % Ce, 1 wt. % Ba, and 0.1 wt. % Fe.

An Al$_2$O$_3$—SiO$_2$ support including 10% SiO$_2$ (Sasol Siralox 10) was impregnated with an aqueous solution of Ga(NO$_3$)$_3$, Pt(NH$_3$)$_4$(NO$_3$)$_2$, KNO$_3$, Ce(NO$_3$)$_3$·6H$_2$O, Ba(NO$_3$)$_2$ and Cu(NO$_3$)$_2$·5H$_2$O by incipient wetness. The impregnated support was dried in air at room temperature for at least 1 hour, then dried in air at 338° F. for 1 hour, and then calcined in air at 1382° F. for 1 hour, to provide catalyst A7 comprising 4.5 wt. % Ga, 0.02 wt. % Pt, 0.25 wt. % K, 1 wt. % Ce, 1 wt. % Ba, and 0.1 wt. % Cu.

An Al$_2$O$_3$—SiO$_2$ support including 10% SiO$_2$ (Sasol Siralox 10) was impregnated with an aqueous solution of Ga(NO$_3$)$_3$, Pt(NH$_3$)$_4$(NO$_3$)$_2$, KNO$_3$, Ce(NO$_3$)$_3$·6H$_2$O, Ba(NO$_3$)$_2$ and SnCl$_4$·4H$_2$O by incipient wetness. The impregnated support was dried in air at room temperature for at least 1 hour, then dried in air at 338° F. for 1 hour, and then calcined in air at 1382° F. for 1 hour, to provide catalyst A8 comprising 4.5 wt. % Ga, 0.02 wt. % Pt, 0.25 wt. % K, 1 wt. % Ce, 1 wt. % Ba, and 0.05 wt. % Sn.

An Al$_2$O$_3$—SiO$_2$ support including 10% SiO$_2$ (Sasol Siralox 10) was impregnated with an aqueous solution of Ga(NO$_3$)$_3$, Pt(NH$_3$)$_4$(NO$_3$)$_2$, KNO$_3$, Ce(NO$_3$)$_3$·6H$_2$O, Ba(NO$_3$)$_2$ and La(NO$_3$)$_3$·6H$_2$O by incipient wetness. The impregnated support was dried in air at room temperature for at least 1 hour, and then calcined in air at 338° F. for 1 hour and at 1382° F. for 1 hour, to provide catalyst A9 comprising 4.5 wt. % Ga, 0.02 wt. % Pt, 0.25 wt. % K, 1 wt. % Ce, 1 wt. % Ba, and 1.2 wt. % La.

An Al$_2$O$_3$—SiO$_2$ support including 10% SiO$_2$ (Sasol Siralox 10) was impregnated with an aqueous solution of Ga(NO$_3$)$_3$, Pt(NH$_3$)$_4$(NO$_3$)$_2$, KNO$_3$, Ce(NO$_3$)$_3$·6H$_2$O, and La(NO$_3$)$_3$·6H$_2$O by incipient wetness. The impregnated support was dried in air at room temperature for at least 1 hour, then dried in air at 338° F. for 1 hour, and then calcined in air at 1382° F. for 1 hour, to provide catalyst A10 comprising 4.5 wt. % Ga, 0.02 wt. % Pt, 0.25 wt. % K, 1.5 wt. % Ce, and 1.2 wt. % La.

An Al$_2$O$_3$—SiO$_2$ support including 10% SiO$_2$ (Sasol Siralox 10) was first impregnated with an aqueous solution of Ce(NO$_3$)$_3$·6H$_2$O by incipient wetness. The impregnated support was dried in air at room temperature for at least 1 hour, then dried in air at 338° F. for 1 hour, and then calcined in air at 1382° F. for 1 hour, to provide a Ce-containing support comprising 2 wt. % Ce. The Ce-containing support was then impregnated with an aqueous solution of Ga(NO$_3$)$_3$, Pt(NH$_3$)$_4$(NO$_3$)$_2$, KNO$_3$, Ce(NO$_3$)$_3$·6H$_2$O, and La(NO$_3$)$_3$·6H$_2$O by incipient wetness. The impregnated support was dried in air at room temperature for at least 1 hour, then dried in air at 338° F. for 1 hour, and then calcined in air at 1382° F. for 1 hour, to provide catalyst A11 comprising 4.5 wt. % Ga, 0.02 wt. % Pt, 0.25 wt. % K, 3 wt. % Ce, and 1 wt. % Ba.

An Al$_2$O$_3$—SiO$_2$ support including 10% SiO$_2$ (Sasol Siralox 10) was first impregnated with an aqueous solution of Zn(NO$_3$)$_2$ by incipient wetness. The impregnated support was dried in air at room temperature for at least 1 hour, then dried in air at 338° F. for 1 hour, and then calcined in air at 1382° F. for 1 hour, to provide a Zn-containing support comprising 2 wt. % Zn. The Zn-containing support was then impregnated with an aqueous solution of Ga(NO$_3$)$_3$, Pt(NH$_3$)$_4$(NO$_3$)$_2$, KNO$_3$, Ce(NO$_3$)$_3$·6H$_2$O, and La(NO$_3$)$_3$·6H$_2$O by incipient wetness. The impregnated support was dried in air at room temperature for at least 1 hour, then dried in air at 338° F. for 1 hour, and then calcined in air at 1382° F. for 1 hour, to provide catalyst A12 comprising 4.5 wt. % Ga, 0.02 wt. % Pt, 0.25 wt. % K, 1 wt. % Ce, 1 wt. % Ba, and 2 wt. % Zn.

An Al$_2$O$_3$—SiO$_2$ support including 5% SiO$_2$ (Sasol Siralox 5) was impregnated with an aqueous solution of Ga(NO$_3$)$_3$, Pt(NH$_3$)$_4$(NO$_3$)$_2$, KNO$_3$, Ce(NO$_3$)$_3$·6H$_2$O, and Ba(NO$_3$)$_2$ by incipient wetness. The impregnated support was dried in air at room temperature for at least 1 hour, then dried in air at 338° F. for 1 hour, and then calcined in air at 1382° F. for 1 hour, to provide catalyst A13 comprising 4.5 wt. % Ga, 0.02 wt. % Pt, 0.25 wt. % K, 1 wt. % Ce, and 1 wt. % Ba.

Comparative catalysts C4 (lacking Pt), C5 and C6 (zirconia-supported) were similarly prepared. A comparative alumina-supported chromium catalyst C3 was prepared according to conventional methods.

TABLE 1

Catalyst Compositions

| Cat. | SiO$_2$ (wt. %) | Al$_2$O$_3$ (wt. %) | ZrO$_2$ (wt. %) | La$_2$O$_3$ (wt. %) | W (wt. %) |
|---|---|---|---|---|---|
| C1 | 0 | 100 | | | |
| C2 | 10 | 90 | | | |
| C4 | 10 | 90 | | | |
| C5 | | | 90 | 10 | |
| C6 | | | 84 | | 16 |
| A1 | 10 | 90 | | | |
| A2 | 10 | 90 | | | |
| A3 | 10 | 90 | | | |
| A4 | 10 | 90 | | | |
| A5 | 10 | 90 | | | |
| A6 | 10 | 90 | | | |
| A7 | 10 | 90 | | | |
| A8 | 10 | 90 | | | |
| A9 | 10 | 90 | | | |
| A10 | 10 | 90 | | | |
| A11 | 10 | 90 | | | |
| A12 | 10 | 90 | | | |
| A13 | 5 | 95 | | | |

TABLE 2

Catalyst Compositions (continued)

| Cat. | Ga (wt. %) | Ce (wt. %) | Pt (ppm) | K (wt. %) | Ba (wt. %) | Other |
|---|---|---|---|---|---|---|
| C1 | 3 | | 0.025 | 0.35 | | |
| C2 | 4.5 | | 0.02 | 0.25 | | |
| C4 | 4.5 | 1 | | 0.25 | 1 | |
| C5 | 4.5 | 1 | 0.02 | 0.25 | | |
| C6 | 4.5 | 1 | 0.02 | 0.25 | | |
| A1 | 4.5 | 1 | 0.02 | 0.25 | | |
| A2 | 4.5 | 1 | 0.02 | 0.25 | 1 | |
| A3 | 4.5 | 1 | 0.02 | 0.25 | | 1.2 wt. % La |
| A4 | 4.5 | 1 | 0.02 | 0.25 | | 1 wt. % Mn |
| A5 | 4.5 | 1 | 0.02 | 0.25 | | 0.3 wt. % Ti |
| A6 | 4.5 | 1 | 0.02 | 0.25 | 1 | 0.1 wt. % Fe |
| A7 | 4.5 | 1 | 0.02 | 0.25 | 1 | 0.1 wt. % Cu |
| A8 | 4.5 | 1 | 0.02 | 0.25 | 1 | 0.05 wt. % Sn |
| A9 | 4.5 | 1 | 0.02 | 0.25 | 0.5 | 1.2 wt. % La |
| A10 | 4.5 | 1.5 | 0.02 | 0.25 | | 1.2 wt. % La |
| A11 | 4.5 | 3 | 0.01 | 0.25 | 1 | |
| A12 | 4.5 | 1 | 0.01 | 0.25 | 1 | 2 wt. % Zn |
| A13 | 4.5 | 1 | 0.02 | 0.25 | 1 | |

Example 2. Propane Dehydrogenation

Catalyst compositions prepared according to Example 1 were tested as prepared in a fixed-bed reactor. A feed containing 100 mol. % propane was passed over a catalyst bed at a total pressure of 0.5 atm., at 2.0 h$^{-1}$ liquid hourly space velocity (LHSV), at a temperature within the range of 540-600° C. in cyclic mode, where 10 minutes of propane dehydrogenation is followed by catalyst regeneration in air. Results are provided in Table 3, below.

TABLE 3

Propane Dehydrogenation

| Cat. | Cycle no. | Conversion (wt. %) | Selectivity (wt. %) | Yield (wt. %) |
| --- | --- | --- | --- | --- |
| C3 | 1 | 33.04 | 87.02 | 28.75 |
| C3 | 50 | 46.29 | 84.06 | 38.94 |
| C1 | 1 | 58.7 | 78.25 | 45.91 |
| C1 | 50 | 27.8 | 91.1 | 25.3 |
| C2 | 1 | 34.7 | 89.9 | 31.2 |
| C2 | 50 | 43.2 | 87.2 | 37.7 |
| C4 | 1 | 28.6 | 89.1 | 25.5 |
| C4 | 100 | 36.7 | 91.2 | 33.5 |
| C5 | 1 | 20.9 | 56.6 | 11.8 |
| C5 | 30 | 18.8 | 53.0 | 10.0 |
| C6 | 1 | 41.9 | 69.4 | 29.1 |
| C6 | 25 | 36.6 | 71.1 | 26.0 |
| A1 | 1 | 34.5 | 91.4 | 31.6 |
| A1 | 50 | 46.4 | 88.7 | 41.1 |
| A2 | 1 | 58.1 | 84.9 | 49.3 |
| A2 | 50 | 34.9 | 90.5 | 31.5 |
| A3 | 1 | 42.8 | 88.6 | 37.9 |
| A3 | 50 | 51.1 | 84.2 | 43 |
| A4 | 1 | 33.2 | 91.6 | 30.4 |
| A4 | 50 | 40.6 | 90.3 | 36.6 |
| A5 | 1 | 48.7 | 86.7 | 42.2 |
| A5 | 50 | 36.48 | 89.72 | 32.72 |
| A9 | 1 | 46.79 | 88.38 | 41.38 |
| A9 | 50 | 57.8 | 84.23 | 48.67 |
| A10 | 1 | 36.12 | 91.02 | 32.88 |
| A10 | 50 | 45.23 | 89.4 | 40.45 |
| A11 | 15 | 55.19 | 84.74 | 46.74 |
| A11 | 95 | 31.88 | 90.73 | 28.91 |
| A12 | 15 | 41.41 | 89.63 | 37.13 |
| A12 | 100 | 51.64 | 86.87 | 44.83 |
| A13 | 1 | 37.53 | 88.05 | 33.05 |
| A13 | 95 | 47.77 | 87.23 | 41.68 |

The results show that the performance of the catalysts tested was acceptable, providing good yields, selectivity and conversion even in the absence of chromium, and even over comparative gallium-containing catalysts. For example, the results show that catalyst A9 is especially stable, and that catalyst A13 is highly selective.

Additional aspects of the disclosure are provided by the following enumerated embodiments, which can be combined in any number and in any fashion that is not technically or logically inconsistent.

Embodiment 1. A dehydrogenation catalyst composition comprising
  Ga, present in the composition in an amount within the range of 0.5 wt. % to 20 wt. %, calculated as elemental metal on a calcined basis;
  Ce, present in the composition in an amount within the range of 0.2 wt. % to 20 wt. %, calculated as elemental metal on a calcined basis;
  Pt, present in the composition in an amount within the range of 1 ppm to 500 ppm, calculated as elemental metal on a calcined basis;
  optionally, a promoter M2 selected from the alkali metals, the alkaline earth metals, and any mixture thereof, present in the composition in an amount of up to 20 wt. %, calculated as elemental metal on a calcined basis; and
  a silica-alumina support S1, present in the composition in an amount within the range of 50 wt. % to 99 wt. %, calculated as oxide on a calcined basis, silica being present in S1 in an amount within the range of 1 wt. % to 30 wt. %, calculated as $SiO_2$ on a calcined basis.

Embodiment 2. The catalyst composition of embodiment 1, wherein Ga is present in the composition in an amount within the range of 0.5 wt. % to 15 wt. %, e.g., 0.5 wt. % to 12.5 wt. %, or 0.5 wt. % to 10 wt. %, or 0.5 wt. % to 8.5 wt. %, or 0.5 wt. % to 7 wt. %, or 0.5 wt. % to 5 wt. %, calculated as elemental metal on a calcined basis.

Embodiment 3. The catalyst composition of embodiment 1, wherein Ga is present in the composition in an amount within the range of 0.5 wt. % to 10 wt. %, e.g., 0.5 wt. % to 8.5 wt. %, or 0.5 wt. % to 7 wt. %, or 0.5 wt. % to 5 wt. %, or 0.5 wt. % to 3 wt. %, calculated as elemental metal on a calcined basis.

Embodiment 4. The catalyst composition of embodiment 1, wherein Ga is present in the composition in an amount within the range of 1 wt. % to 10 wt. %, e.g., 1 wt. % to 8.5 wt. %, or 1 wt. % to 7 wt. %, or 1 wt. % to 5 wt. %, or 1 wt. % to 3 wt. %, calculated as elemental metal on a calcined basis.

Embodiment 5. The catalyst composition of embodiment 1, wherein Ga is present in the composition in an amount within the range of 1.5 wt. % to 10 wt. %, e.g., 1.5 wt. % to 8.5 wt. %, or 1.5 wt. % to 7 wt. %, or 1.5 wt. % to 5 wt. %, or 1.5 wt. % to 3 wt. %, calculated as elemental metal on a calcined basis.

Embodiment 6. The catalyst composition of embodiment 1, wherein Ga is present in the composition in an amount within the range of 2 wt. % to 10 wt. %, e.g., 2 wt. % to 8.5 wt. %, or 2 wt. % to 7 wt. %, or 2 wt. % to 5 wt. %, or 2 wt. % to 5 wt. %, calculated as elemental metal on a calcined basis.

Embodiment 7. The catalyst composition of embodiment 1, wherein Ga is present in the composition in an amount within the range of 3 wt. % to 10 wt. %, e.g., 3 wt. % to 8.5 wt. %, or 3 wt. % to 7 wt. %, or 3 wt. % to 5 wt. %, or 3 wt. % to 5 wt. %, calculated as elemental metal on a calcined basis.

Embodiment 8. The catalyst composition of any of embodiments 1-7, wherein Ce is present in the composition in an amount of 0.2 wt. % to 15 wt. %, e.g., 0.2 wt. % to 10 wt. %, or 0.2 wt. % to 7 wt. %, or 0.2 wt. % to 5 wt. %, or 0.2 to 3 wt. %, calculated as elemental metal on a calcined basis.

Embodiment 9. The catalyst composition of any of embodiments 1-7, wherein Ce is present in the composition in an amount of 0.5 wt. % to 20 wt. %, e.g., 0.5 wt. % to 15 wt. %, or 0.5 wt. % to 10 wt. %, or 0.5 wt. % to 7 wt. %, or 0.5 wt. % to 5 wt. %, or 0.5 wt. % to 3 wt. %, calculated as elemental metal on a calcined basis.

Embodiment 10. The catalyst composition of any of embodiments 1-7, wherein Ce is present in the composition in an amount of 1 wt. % to 20 wt. %, e.g., 1 wt. % to 15 wt. %, or 1 wt. % to 10 wt. %, or 1 wt. % to 7 wt. %, or 1 wt. % to 5 wt. %, or 1 wt. % to 3 wt. %, calculated as elemental metal on a calcined basis.

Embodiment 11. The catalyst composition of any of embodiments 1-10, wherein Pt is present in the composition in an amount within the range of 5 ppm to 500 ppm, e.g., 25 ppm to 500 ppm, or 100 ppm to 500 ppm, calculated as elemental metal on a calcined basis.

Embodiment 12. The catalyst composition of any of embodiments 1-10, wherein Pt is present in the composition in an amount within the range of 1 ppm to 450 ppm, e.g., 5 ppm to 450 ppm, or 25 ppm to 450 ppm, or 100 ppm to 450 ppm, calculated as elemental metal on a calcined basis.

Embodiment 13. The catalyst composition of any of embodiments 1-10, wherein Pt is present in the composition in an amount within the range of 1 ppm to 400 ppm, e.g., 5 ppm to 400 ppm, or 25 ppm to 400 ppm, or 100 ppm to 400 ppm, calculated as elemental metal on a calcined basis.

Embodiment 14. The catalyst composition of any of embodiments 1-10, wherein Pt is present in the composition in an amount within the range of 1 ppm to 350 ppm, e.g., 5 ppm to 350 ppm, or 25 ppm to 350 ppm, or 100 ppm to 350 ppm, calculated as elemental metal on a calcined basis.

Embodiment 15. The catalyst composition of any of embodiments 1-10, wherein Pt is present in the composition in an amount within the range of 1 ppm to 300 ppm, e.g., 5 ppm to 300 ppm, or 25 ppm to 300 ppm, or 100 ppm to 300 ppm, calculated as elemental metal on a calcined basis.

Embodiment 16. The catalyst composition of any of embodiments 1-15, wherein M2 includes one or more alkali metals, present in the composition in a combined amount within the range of 0.2 wt. % to 2.5 wt. %.

Embodiment 17. The catalyst composition of any of embodiments 1-16, wherein M2 includes K.

Embodiment 18. The catalyst composition of any of embodiments 1-17, wherein M2 includes one or more alkaline earth metals, present in the composition in a combined amount within the range of 0.2 wt. % to 10 wt. %.

Embodiment 19. The catalyst composition of any of embodiments 1-18, wherein M2 includes Ba.

Embodiment 20. The catalyst composition of any of embodiments 1-19, wherein silica is present in S1 in an amount within the range of 2 wt. % to 20 wt. % of S1.

Embodiment 21. The catalyst composition of any of embodiments 1-20, wherein alumina is present in S1 in an amount within the range of 70 wt. % to 99 wt. %, calculated as $Al_2O_3$ on a calcined basis.

Embodiment 22. The catalyst composition of any of embodiments 1-21, wherein the support S1 is present in the composition in an amount within the range of 50 wt. % to 98 wt. %.

Embodiment 23. The catalyst composition of any of embodiments 1-22, further comprising one or more of La, Mn, Ti, Fe, Cu, Sn, W, Y, and Zn, present in the composition in a combined amount within the range of 0.01 wt. % to 10 wt. %.

Embodiment 24. The catalyst composition of any of embodiments 1, 8-10 and 16-21, wherein Ga is present in an amount of 2 to 10 wt. %, and Pt is present in an amount of 10 ppm to 400 ppm Embodiment 25. The catalyst composition of any of embodiments 1 and 16-21, wherein
  Ga is present in the composition in an amount within the range of 1 wt. % to 5 wt. %, e.g., 2 wt. % to 5 wt. %;
  Ce is present in the composition in an amount within the range of 1 wt. % to 10 wt. %, e.g., 1 wt. % to 5 wt. %;
  Pt is present in the composition in an amount within the range of 10 ppm to 500 ppm, e.g., 10 ppm to 400 ppm; and
  S1 is present in the composition in an amount within the range of 80 wt. % to 99 wt. %.

Embodiment 26. The catalyst composition of embodiment 25, wherein silica is present in S1 in an amount within the range of 2 wt. % to 20 wt. %.

Embodiment 27. The catalyst composition of embodiment 25 or embodiment 26, wherein M2 is K, present in the composition in an amount within the range of 0.2 wt. % to 2.5 wt. %.

Embodiment 28. The catalyst composition of embodiment 25 or embodiment 26, wherein M2 is a mixture of K and Ba, present in the composition in a combined amount within the range of 0.5 wt. % to 5 wt. %.

Embodiment 29. The catalyst composition of any of embodiments 25-28, comprising one or more of La, Mn, Ti, Fe, Cu, Sn, and Zn, present in the composition in a combined amount within the range of 0.01 wt. % to 10 wt. %.

Embodiment 30. The catalyst composition of embodiment 1 or embodiment 23, wherein
  Ga is present in the composition in an amount within the range of 2 wt. % to 5 wt. %, e.g., 3 wt. % to 5 wt. %;
  Ce is present in the composition in an amount within the range of 1 wt. % to 5 wt. %;
  Pt is present in the composition in an amount within the range of 100 ppm to 500 ppm, e.g., 100 ppm to 400 ppm;
  M2 is a mixture of K and Ba, present in the composition in a combined amount within the range of 0.5 wt. % to 5 wt. %;
  S1 is present in the composition in an amount within the range of 90 wt. % to 99 wt. %; and
  silica is present in S1 in an amount within the range of 2 wt. % to 20 wt. %.

Embodiment 31. The catalyst composition of embodiment 30, further comprising La, present in the composition in an amount within the range of 0.1 wt. % to 5 wt. %.

Embodiment 32. The catalyst composition of embodiment 1 or embodiment 23, wherein
  Ga is present in the composition in an amount within the range of 2 wt. % to 5 wt. %, e.g., 3 wt. % to 5 wt. %;
  Ce is present in the composition in an amount within the range of 1 wt. % to 5 wt. %;
  Pt is present in the composition in an amount within the range of 100 ppm to 500 ppm, e.g., 100 ppm to 400 ppm;
  M2 is a mixture of K and Ba, present in the composition in a combined amount within the range of 1 wt. % to 5 wt. %;
  S1 is present in the composition in an amount within the range of 90 wt. % to 99 wt. %; and
  silica is present in S1 in an amount within the range of 2 wt. % to 20 wt. %.

Embodiment 33. The catalyst composition of embodiment 32, further comprising Fe, present in the composition in an amount within the range of 0.025 wt. % to 1.5 wt. %.

Embodiment 34. The catalyst composition of embodiment 32, further comprising Sn, present in the composition in an amount within the range of 0.01 wt. % to 1 wt. %.

Embodiment 35. The catalyst composition of embodiment 32, further comprising Zn, present in the composition in an amount within the range of 1 wt. % to 6 wt. %.

Embodiment 36. The catalyst composition of embodiment 1 or embodiment 23, wherein
  Ga is present in the composition in an amount within the range of 2 wt. % to 5 wt. %, e.g., 3 wt. % to 5 wt. %;
  Ce is present in the composition in an amount within the range of 1 wt. % to 5 wt. %;
  Pt is present in the composition in an amount within the range of 100 ppm to 500 ppm, e.g., 100 ppm to 400 ppm;
  M2 is K, present in the composition in a combined amount within the range of 0.2 wt. % to 2.5 wt. %;
  S1 is present in the composition in an amount within the range of 90 wt. % to 99 wt. %; and
  silica is present in S1 in an amount within the range of 2 wt. % to 20 wt. %.

Embodiment 37. The catalyst composition of embodiment 36, further comprising La, present in the composition in an amount within the range of 0.1 wt. % to 5 wt. %.

Embodiment 38. The catalyst composition of embodiment 36, further comprising Ti, present in the composition in an amount within the range of 0.05 wt. % to 2 wt. %.

Embodiment 39. The catalyst composition of embodiment 1 or embodiment 23, wherein
Ga is present in the composition in an amount within the range of 2 wt. % to 5 wt. %, e.g., 3 wt. % to 5 wt. %;
Ce is present in the composition in an amount within the range of 1.5 wt. % to 5.5 wt. %;
Pt is present in the composition in an amount within the range of 100 ppm to 500 ppm, e.g., 100 ppm to 400 ppm;
M2 is K, present in the composition in a combined amount within the range of 0.2 wt. % to 2.5 wt. %;
S1 is present in the composition in an amount within the range of 90 wt. % to 99 wt. %; and
silica is present in S1 in an amount within the range of 2 wt. % to 20 wt. %.

Embodiment 40. The catalyst composition of embodiment 39, further comprising La, present in the composition in an amount within the range of 0.1 wt. % to 5 wt. %.

Embodiment 41. The catalyst composition of any of embodiments 1-40, wherein the total amount of Ga, Ce, Pt, M2 and S1 is at least 80 wt. %, e.g., at least 85 wt. %, or at least 87 wt. %, or at least 90 wt. % of the composition.

Embodiment 42. The catalyst composition of embodiment any of embodiments 1-40, wherein the total amount of Ga, Ce, Pt, M2, S1, and any of La, Mn, Ti, Fe, Cu, Sn, W, Y, and Zn present in the composition is at least 85 wt. %, e.g., at least 87 wt. %, or at least 90 wt. %, or at least 92.5 wt. %, or at least 95 wt. %, or at least 97.5 wt. %, or at least 98 wt. % of the composition.

Embodiment 43. A method for preparing a dehydrogenation catalyst composition according to any of embodiments 1-42, comprising
providing a silica-alumina support S1, optionally impregnated with one or more of Ga, Ce, Pt, and M2;
impregnating the silica-alumina support S1 with an impregnation solution comprising one or more of
a Ga source;
a Ce source;
a Pt source; and
optionally, an M2 source; and
calcining the impregnated silica-alumina support S1.

Embodiment 44. A method according to embodiment 43, wherein providing a silica-alumina support S1 comprises reacting an S1 source.

Embodiment 45. A method according to embodiment 44, wherein the reaction is a hydrolysis-polycondensation reaction, and the S1 source comprises one or more metal oxy compounds.

Embodiment 46. A method according to embodiment 44 or 45, wherein providing a silica-alumina support S1 impregnated with one or more of Ga, Ce, Pt, and M2 comprises reacting an S1 source in the presence of one or more of a Ga source, Ce source, Pt source, and M2 source, and calcining the reaction product (e.g., at a temperature within the range of 500-1,200° C., for a period of 2-4 hours).

Embodiment 47. A method according to embodiment 44 or 45, wherein providing a silica-alumina support S1 impregnated with one or both of a Ga source and a Ce source comprises reacting an S1 source in the presence of one or both of a Ga source and a Ce source, and calcining the reaction product (e.g., at a temperature within the range of 500-1,200° C., for a period of 2-4 hours).

Embodiment 48. A method according to any of embodiments 43-47, wherein the calcination temperature is within the range of 500-1,200° C.

Embodiment 49. A method according to any of embodiments 43-48, wherein calcination is conducted for a period of 2-4 hours.

Embodiment 50. A method according to any of embodiments 43-49, further comprising, before calcining the impregnated silica-alumina support S1, drying the impregnated silica-alumina support (e.g., at a temperature within the range of 50-250° C., for a period of 30 minutes to 4 hours).

Embodiment 51. A method for dehydrogenating hydrocarbons, the method comprising contacting a hydrocarbon feed with the catalyst composition of any of embodiments 1-42.

Embodiment 52. The method of embodiment 51, operated at a conversion of at least 25 wt. %, e.g., at least 30 wt. %, at least 40 wt. %, or even at least 45 wt. %.

Embodiment 53. The method of embodiment 51, operated at a conversion in the range of 25-70 wt. %, e.g., 25-60 wt. %, or 25-50 wt. %, or 30-70 wt. %, or 30-60 wt. %, or 30-50 wt. %, or 40-70 wt. %, or 40-65 wt. %, or 40-50 wt. %, or 45-70 wt. %, or 45-65 wt. %, or 45-55 wt. %

Embodiment 54. The method of any of embodiments 51-53, operated at a selectivity of at least 80 wt. %, e.g., at least 85 wt. %, or even at least 90 wt. %.

Embodiment 55. The method of any of embodiments 51-53, operated at a selectivity in the range of 80-95 wt. %, e.g., 80-90 wt. %, or 85-95 wt. %, or 85-90 wt. %, or 90-95 wt. %.

Embodiment 56. The method of any of embodiments 51-55, operated at a yield in the range of 25-55 wt. %, e.g., 25-50 wt. %, or 25-45 wt. %, or 30-55 wt. %, or 30-45 wt. %, or 30-40 wt. %, or 35-55 wt. %, or 35-50 wt. %, or 35-45 wt. %, or 40-55 wt. %, or 40-50 wt. %.

Embodiment 57. The method of any of embodiments 51-56, carried out at a temperature within the range of 400° C. to 850° C.

Embodiment 58. The method of any of embodiments 51-57, carried out at a pressure within the range of 0.1 bar to 1 bar.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

What is claimed is:

1. A dehydrogenation catalyst composition comprising
Ga, present in the composition in an amount within a range of 2 wt. % to 20 wt. %, calculated as elemental metal on a calcined basis;
Ce, present in the composition in an amount within a range of 0.5 wt. % to 10 wt. %, calculated as elemental metal on a calcined basis;

Pt, present in the composition in an amount within a range of 1 ppm to 500 ppm, calculated as elemental metal on a calcined basis;

a promoter M2 selected from the alkali metals, the alkaline earth metals, and any mixture thereof, present in the composition in an amount of up to 7.5 wt. %, calculated as elemental metal on a calcined basis; and a silica-alumina support S1, present in the composition in an amount within a range of 50 wt. % to 97.5 wt. % of the composition, calculated as oxide on a calcined basis, silica being present in S1 in an amount within a range of 5 wt. % to 30 wt. % of the mass of S1, calculated as $SiO_2$ on a calcined basis, wherein amounts of Ga, Ce, Pt, and promoter M2, are provided on the basis of the amount of the support S1 being 100 wt %.

2. The catalyst composition of claim 1, wherein Ga is present in the composition in an amount within a range of 2 wt. % to 10 wt. % calculated as elemental metal on a calcined basis.

3. The catalyst composition of claim 1, wherein Ce is present in the composition in an amount of 0.5 wt. % to 7 wt. % calculated as elemental metal on a calcined basis.

4. The catalyst composition of claim 1, wherein Pt is present in the composition in an amount within a range of 1 ppm to 400 ppm, calculated as elemental metal on a calcined basis.

5. The catalyst composition of claim 1, wherein M2 includes one or more alkali metals, present in the composition in a combined amount within a range of 0.2 wt. % to 2.5 wt. %.

6. The catalyst composition of claim 1, wherein M2 includes K.

7. The catalyst composition of claim 1, wherein alumina is present in S1 in an amount within a range of 70 wt. % to 95 wt. %, calculated as $Al_2O_3$ on a calcined basis.

8. The catalyst composition of any claim 1, further comprising one or more of La, Mn, Ti, Fe, Cu, Sn, W, Y, and Zn, present in the composition in a combined amount within a range of 0.01 wt. % to 10 wt. %.

9. The catalyst composition of claim 1, wherein Ga is present in an amount of 2 to 10 wt. %, and Pt is present in an amount of 5 ppm to 400 ppm.

10. The catalyst composition of claim 1, wherein

Ga is present in the composition in an amount within a range of 2 wt. % to 5 wt. %;

Ce is present in the composition in an amount within a range of 1 wt. % to 10 wt. %; and Pt is present in the composition in an amount within a range of 10 ppm to 500 ppm.

11. The catalyst composition of claim 10, wherein M2 is K, present in the composition in an amount within a range of 0.2 wt. % to 2.5 wt. %.

12. The catalyst composition of claim 10, comprising one or more of La, Mn, Ti, Fe, Cu, Sn, and Zn, present in the composition in a combined amount within a range of 0.01 wt. % to 10 wt. %.

13. The catalyst composition of claim 12, wherein M2 includes one or more alkaline earth metals, present in the composition in a combined amount within a range of 0.2 wt. % to 7.5 wt. %.

14. The catalyst composition of claim 1, wherein

Ga is present in the composition in an amount within a range of 2 wt. % to 5 wt. %;

Ce is present in the composition in an amount within a range of 1 wt. % to 5 wt. %;

Pt is present in the composition in an amount within a range of 100 ppm to 500 ppm;

M2 is a mixture of K and Ba, present in the composition in a combined amount within a range of 0.5 wt. % to 5 wt. %.

15. The catalyst composition of claim 1, wherein the total amount of Ga, Ce, Pt, M2 and S1 and any of La, Mn, Ti, Fe, Cu, Zn, W, Y and Zn is at least 98 wt. % of the composition.

16. The catalyst composition of claim 1, wherein M2 is present in an amount in a range of 0.2 wt. % to 7.5 wt. %.

17. A method for preparing the dehydrogenation catalyst composition according to claim 1, comprising providing a silica-alumina support S1, optionally impregnated with one or more of Ga, Ce, Pt, and M2;

impregnating the silica-alumina support S1 with an impregnation solution comprising one or more of a Ga source;

a Ce source;

a Pt source; and an M2 source; and calcining the impregnated silica-alumina support S1 to obtain the dehydrogenation catalyst composition.

18. A method for dehydrogenating hydrocarbons, the method comprising contacting a hydrocarbon feed with the dehydrogenation catalyst composition of claim 1.

19. The method of claim 18, carried out at a temperature in a range of 400° C. to 850° C.

20. The method of claim 19, operated at a conversion in a range of 25-70 wt. % and a selectivity of at least 80 wt. %.

* * * * *